(12) United States Patent
Rapchak

(10) Patent No.: US 7,002,476 B2
(45) Date of Patent: Feb. 21, 2006

(54) MEDICATION COMPLIANCE SYSTEM

(75) Inventor: Barbara A. Rapchak, Crystal Lake, IL (US)

(73) Assignee: Leap of Faith Technologies, Inc., Crystal Lake, IL (US)

( * ) Notice: Subject to any disclaimer, the term of this patent is extended or adjusted under 35 U.S.C. 154(b) by 162 days.

(21) Appl. No.: 10/718,020

(22) Filed: Nov. 19, 2003

(65) Prior Publication Data
US 2004/0155780 A1 Aug. 12, 2004

Related U.S. Application Data

(60) Provisional application No. 60/443,695, filed on Jan. 30, 2003.

(51) Int. Cl.
G08B 23/00 (2006.01)

(52) U.S. Cl. .............................. 340/573.1; 340/309.16; 340/691.1; 340/691.6

(58) Field of Classification Search ............. 340/691.1, 340/691.6, 573.1, 309.16, 825.19, 666, 309.15; 368/10; 705/2
See application file for complete search history.

(56) References Cited

U.S. PATENT DOCUMENTS

| | | | | |
|---|---|---|---|---|
| 5,963,136 A | * | 10/1999 | O'Brien | 340/573.1 |
| 6,294,999 B1 | * | 9/2001 | Yarin et al. | 340/573.1 |
| 6,507,275 B1 | * | 1/2003 | Romano et al. | 340/309.16 |
| 6,579,231 B1 | * | 6/2003 | Phipps | 600/300 |

* cited by examiner

*Primary Examiner*—Anh V. La
(74) *Attorney, Agent, or Firm*—Welsh & Katz, Ltd.

(57) ABSTRACT

A method and apparatus are provided for facilitating compliance with a medication regimen by a user. The method includes the steps of providing the user with a medication dispensing unit for dispensing medication to the user and a wireless transceiver operatively coupled to a controller of the medication dispensing unit, downloading a set of instructions for controlling the medication unit from a server to the controller of the medication dispensing unit through the wireless transceiver and downloading a set of instructions that instruct the user on how to use the dispensed medication through the wireless transceiver to the user.

39 Claims, 2 Drawing Sheets

MEDICATION COMPLIANCE SYSTEM

CROSS REFERENCE TO RELATED APPLICATIONS

This application claims the benefit of U.S. Provisional Patent Application No. 60/443,695 filed on 30 Jan. 2003.

FIELD OF THE INVENTION

The field of the invention relates to medication of human patients and more particularly to methods of managing and dispensing medication.

BACKGROUND OF THE INVENTION

Medication is a relatively inexpensive and efficient therapeutic strategy for treating a number of illnesses. However, the average rate of compliance for patients on chronic therapies is about 50% after one year and declines over time. Medication noncompliance is estimated to cost the US healthcare system an estimated $76.6 billion a year. Approximately 10% of hospital admissions are related to medication issues, costing up to $50 billion annually.

Understanding the causes of noncompliance and identifying methods to help patients follow their regimens may improve health outcomes and reduce related costs. Health decision models suggest that noncompliant behavior is multifactorial. By modifying general and specific health beliefs, modifying social interaction factors, and enhancing administration, compliance can be improved. The enhanced compliance program proposed herein focuses specifically on modifying social interaction factors and providing a tool to enhance the administration process.

The elderly represent an important population among those receiving drug therapy. They receive 30% of all prescriptions—twice as many as the general population—and they buy 40% of all over-the-counter drugs. In 2000, there were an estimated 35 million people age 65 or older in the United States, accounting for almost 13% of the total population. In 2011, the "baby boom" generation will begin to turn 65, and by 2030, it is projected that 20% of the population will be age 65 or older.

The inability to manage medications is one of the leading reasons why seniors need additional and often more expensive care, such as assisted living facilities or nursing homes: 23% of caregivers report issues associated with medications, 23% of nursing home admissions are related to medication problems and 80% of assisted living residents have medications managed by their facilities. Elderly patients tend to have difficulty complying with or adhering to medication regimens that may tax their cognitive skills. Older adults evidence a decline in a number of cognitive domains and appear to comprehend and remember less about medication information than young adults. In field studies, the oldest segment (those over age 77) were found to be the most nonadherent. Understanding the causes of noncompliance and identifying methods to assist elderly patients in following their regimens may improve health care outcomes.

In general, understanding the reasons for noncompliance provides a basis for reducing the incidence of noncompliance. However, a need still exists for structural methods for helping the elderly conform to prescribed medication regimens.

SUMMARY

A method and apparatus are provided for ensuring compliance with a medication program by a user. The method includes the steps of providing the user with a medication dispensing unit for dispensing medication to the user and a wireless transceiver operatively coupled to a controller of the medication dispensing unit, downloading a set of instructions for controlling the medication unit from a server to the controller of the medication dispensing unit through the wireless transceiver and downloading a set instructions that instructs the user about how to use the dispensed medication through the wireless transceiver to the user.

DETAILED DESCRIPTION OF AN ILLUSTRATED EMBODIMENT

The mechanics of medication compliance involve a simple, yet critical process—safely getting the correct medication into the hands of the patient at the correct time. Any system to facilitate compliance should be designed to remind and monitor, organize, and dispense medications, as well as provide feedback.

Information processing is a critical element in this process. Information processing interventions for medication compliance have been defined to: (1) restructure medication information to make it easier to process, (2) remind patients to take the medication, and (3) organize medications to enhance administration. The system described below provides the intervention that meets the criteria for information processing as well as the mechanics of compliance.

Described below is a fully-integrated, telephone-based, medication compliance system 10. The system ensures compliance with a medication program by reminding individuals to take their medication on schedule, simplifies medication organization and delivery, and monitors and reports on compliance. Under one illustrated embodiment, it consists of a cellular phone-based medication service with refillable dispenser that is integral to or integrated with the phone-thus getting the correct medication into the hands of the patient at the correct time. Under one illustrated embodiment, the phone-based system calls the patient at programmed intervals, gives voice, text, and graphic instructions for taking the medication, and dispenses the medication directly to the patient.

Figure 1:
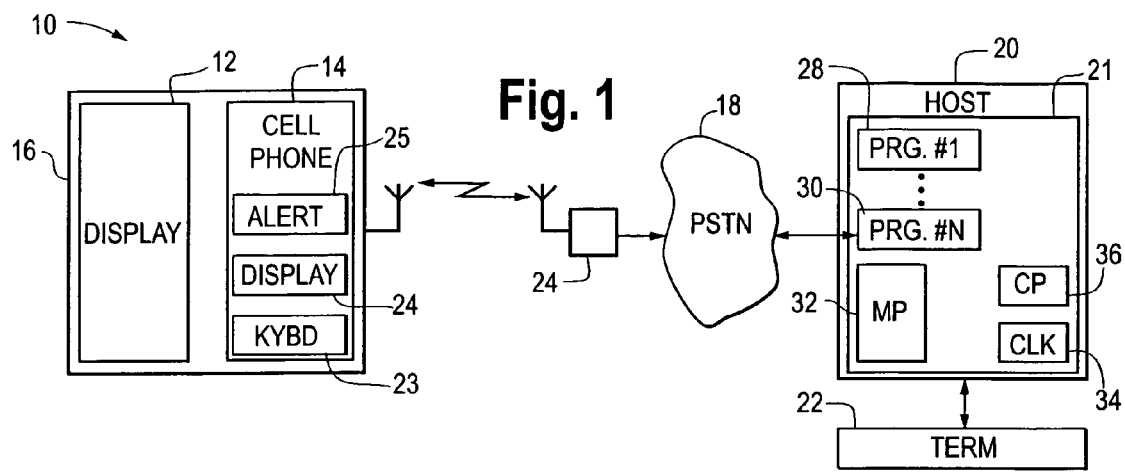
FIG. 1 depicts a medication dispensing system in accordance with an illustrated embodiment of the invention.

FIG. 1 depicts the system 10 for ensuring compliance with a medication program shown in a context of use, generally in accordance with an illustrated embodiment of the invention. The medication compliance system 10 may include a dispensing subsystem (unit) 16 coupled to a server 21 within a host 20 through a cellular base station 24 and the Public Switched Telephone Network (PSTN) 18.

The dispensing unit 16 may be provided as a battery-powered, portable device that may be easily carried in a purse or pocket of a user. The dispensing unit 16 may be provided with a removable dispenser 12 that contains medications and that dispenses medications to the user under control of information downloaded through an attached cellular transceiver 14.

The dispenser 12 may be disposable or refillable. While the dispensing unit 16 will be described in terms of a single dispenser 12, it should be understood that the dispensing unit 16 may be used with multiple dispensers 12 where each dispenser dispenses a different medication.

Further, the term "medication" may mean any therapeutic material that may be dispensed on command. Under one illustrated embodiment, the medication may be provided on a strip of perforated backing material with plastic chambers containing pills disposed at regular intervals along the length of the strip and where the perforation allows the individual medication packets to be removed by tearing across the perforations.

Under an illustrated embodiment, a healthcare worker (not shown) may enter data on the identification and use of the medications into the server 21 through a terminal 22 attached to a host 20. The host 20 (or healthcare worker or patient's doctor) may also forward packaging information to a medication provider (e.g., Cardinal Health, Inc.) that provides the medication in a format that is compatible with the dispenser 12. The medication provider may provide individual, patient-specific, bar-coded (RFID coded), labeled packets that are customized for the patient user. The packets may be provided in dosage strips that are delivered to the user on a regular basis. The size and the shape of the strips may be configured to minimize shipping costs and be optimized for use with the dispenser 12.

Once the medication has been loaded into the dispenser 12, the host 20 may function to remotely control the dispensing unit 16 by downloading instructions to the dispensing unit 16. The downloaded instructions may cause the dispensing unit 16 to dispense medications at prescribed times and also to concurrently instruct the user on the use of the medications.

In addition to controlling the dispensing of the medication, the host 20 may also remotely detect acceptance of the medication by the user and may also detect when the dispensing cartridge 12 is empty. Records on acceptance may be uploaded to the host 20 each time the medication is dispensed or may be uploaded periodically under control of the host 20.

Figure 2:
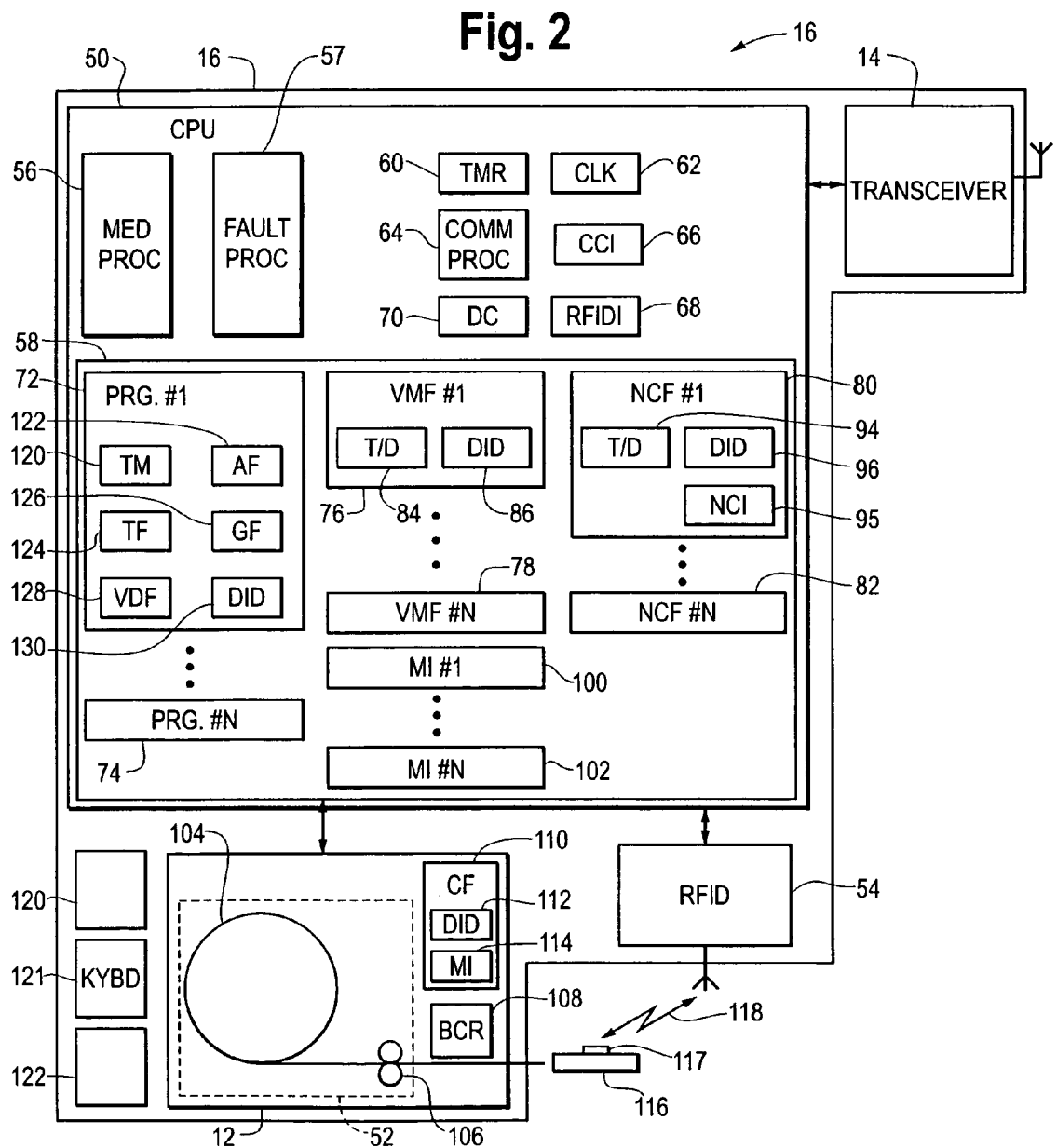
FIG. 2 depicts a portable medication dispensing subsystem that may by used with the system of FIG. 1.
Figure 3:
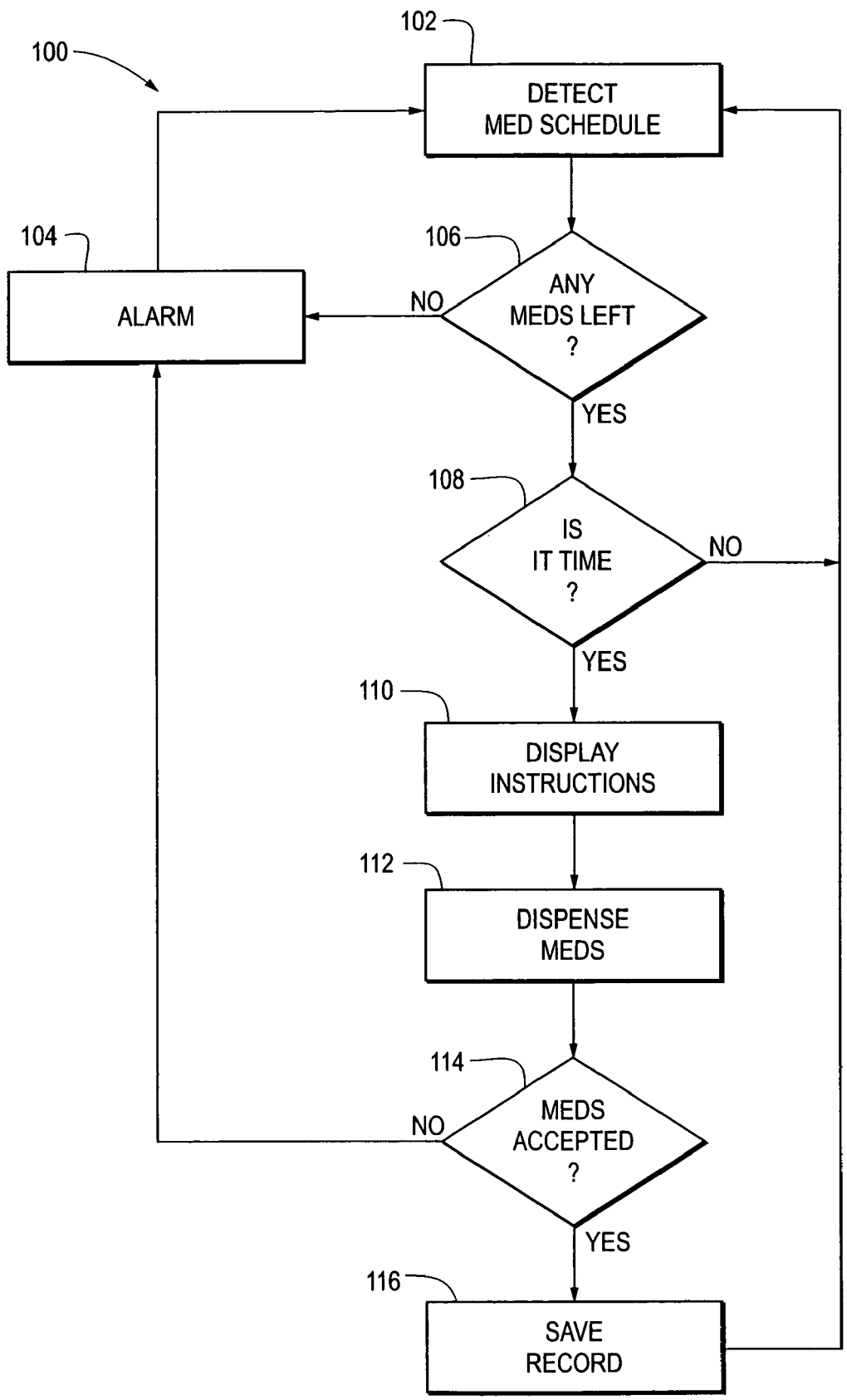
FIG. 3 depicts a flow chart that may be used to describe processes used by the system and subsystem of FIGS. 1 and 2.

Turning now to the system 10, in specific, an explanation will be provided of the operation of the components of the system 10. FIG. 2 is a block diagram of the dispensing unit 16. FIG. 3 is a flow chart that may be used by the system 10 in dispensing medications. Reference shall be made to the figures as appropriate to an understanding of the invention.

It should be noted in passing with regard to FIG. 2 that many of the functions that will be described in conjunction with the central processing unit (CPU) 50 of the dispensing unit 16 could also be performed by the CPU within the cell phone 14. For ease of description, however, the operations performed by the CPU 50 will be described separately from the cell phone 14. It should also be understood however, that instead of a cell phone as shown in FIG. 1, the transceiver 14 shown in FIG. 2 may simply be a circuit card that is disposed within an enclosure of the dispensing unit 16 and that is based upon any wireless technology. In view of the multiplicity of ways in which the wireless interface may be interconnected with the dispenser 16, the explanation provided below will illustrate a number of different possible ways of practicing the invention.

Under a first embodiment of the invention, the dispensing unit 16 may be ultimately controlled by the use of one or more medication files 28, 30 created in the host 20 by the medical care worker working at the terminal 22. Information from the medication files 28, 30, in turn, may be downloaded to the dispensing unit 16. Within the dispensing unit 16, a medication processor 56 may execute a medication routine based upon the information (i.e., the medication schedule) contained within the medication files 28, 30. Executing a medication routine means dispensing the medication 116 by activating an actuator (e.g., a drive motor) while at the same time providing audio/visual information advising the patient on the proper method of using the medication.

The audio/visual information may include text instructions or graphic information appearing on a display 24 of the cellular phone 14 or a display 120 mounted in the dispenser 16. Alternately, the audio/visual information may include verbal instructions provided through an earphone of the cellular telephone 14 or through a electro-acoustic transducer 122 mounted in the dispenser 16.

In order to administer medications, the files 28, 30 created within the host 20 may contain medication information as well as routing information that allows the file 28, 30 to be delivered to the dispensing unit 16. Alternatively, the files 28, 30 may be retained at the host 20 with only portions of the files 28, 30 (i.e., the individual instructions) downloaded to the dispenser 16 and user through the wireless interface.

Information contained in the file 28, 30 may include a communication system identifier (e.g., cellular telephone number of the transceiver 14), a time of medication, a drug identifier and instructions (audio/visual information) for use of the medication. The user instructions for use of the medication may include audio instructions (e.g., provided as a WAV file), text instructions (e.g., provided as a WORD file), graphic instructions (e.g., provided as a jpg file) and timing instructions for operation of an audio/visual alerting device (e.g., a flashing light, vibrator, etc.). The time of medication may be provided under a format defined by a measurable time interval (e.g., every 4 hours, once every 8 hours, etc.) or under a format defined by a 24-hour clock.

Where the dispenser is remotely controlled by the host 20, a server medication processor 32 may periodically scan 102 each file 28, 30 and compare 108 the time of medication with a time of a local clock 34 using an internal comparator. When a match is found, the server medication processor 32 may retrieve a telephone number of the cell phone 14 from the file 28, 30 and transfer the telephone number to a server communication processor 36. The server communication processor 36 may cause a call to be placed to the cell phone 14 attached to the dispenser 16.

The user may answer the call through the cell phone 14 by pressing the SND button. By pressing the SND button on the cell phone 14, a voice channel may be opened between the host 20 and dispenser 16.

Upon detecting that the user has answered the phone 14, the medication controller 32 may retrieve a audible file (e.g., a WAV file) from the record 28, 30 and cause the audible file to be reproduced in audible form through the voice channel for the benefit of the user. The audible message may be instructions for use of the medication (e.g., take the medication with food).

At the same time as the server medication processor 32 places the call to the user, the server medication processor 32 may also retrieve and send text and graphics information to the cell phone 14. The text and graphics may be sent to the display 24 of the cell phone 14 using the instant messaging features of the cell phone and may provide user information regarding the use of the medication as described in more detail below.

As the user is reviewing the instructions regarding the use of the medication, a local medication processor 56 located within the dispenser 16 may monitor the voice channel through a local communication processor 64. During this time, the medication processor 32 within the server 21 may transfer instructions from the file 28, 30 to the local medication processor 56 through the voice channel using an appropriate signaling technology (e.g., subaudible signaling, blank-and-burst, etc.). The instructions transferred may cause the local medication processor 56 to dispense 112 the medication 116 to the user.

Alternatively, the server medication processor 32 may also transfer instructions from the file 28, 30 or portions of the file to the dispenser 16 without using a voice channel. In general, the communication link used between the host 20 and medication unit 16 may be based upon any appropriate technology. For example, the medication instructions could be formatted and transferred through a control channel monitored by the cellular transceiver 14. Alternately, the transceiver portion 14 may be based upon the use of wireless local area network (WLAN) technology using a palm pilot or equivalent technology and the link between the medication unit 16 and host 20 may be, in part, through the Internet.

In addition, the transferred file may be encoded as appropriate for the link. For example, where the file 28, 30 is transferred to the dispensing unit 16, the file 28, 30 may be first encoded under a TCP/IP format for transfer through a Local Area Network (LAN) associated with the host 20 and then further encoded within a gateway under an encapsulation protocol (e.g., Point-to-Point Protocol (PPP)) to accommodate the wireless interface.

In operation, the medication unit 16 may continuously monitor the communication channel (e.g., the cellular control channel) to detect messages addressed to the unit 16. Detection may occur by matching an internal telephone number of the transceiver 14 with a telephone numbers of detected messages.

Upon detecting a medication alert message, the transceiver 14 may transfer the message through a communication channel interface 66 and communication processor 64 to a medication processor 56. The communication channel interface 66 may function to remove any formatting associated with the wireless channel (e.g., PPP). Similarly, the communication processor may function to recover the program file 28, 30 from the TCP/IP formatting added by the host 20.

Upon receipt of the medication alert message, the medication processor 56 may process the file 28, 30 immediately or store the file 28, 30 (now identified in FIG. 2 by reference number 72) for later processing. Included within the file 72 may be a medication time 120, a audio file 122, a text file 124, a graphics file 126, a video device file 128 and a drug identifier 130.

The medication processor 56 may first compare the drug identifier 130 with a drug identifier 112 provided with the dispenser 12. If the drug identifier 112 of the dispenser 52 does not match the drug identifier 130 of the medication file 72, then the medication processor 56 may return an error message (as described below) to the host 20.

If the drug identifier 112 on the dispenser 52 does match the identifier 130 of the medication file 72, then the medication processor 56 may also alert the user to the need to take the medication and to provide instructions on the use of the medication. To alert the user, the medication processor 56 may activate an alerting device 122. The alerting device 122 may be an audible tone generating device or a blinking light.

The user may respond to the alert by activating an ACKNOWLEDGE button on a keyboard 121 of the dispensing unit 16. In response, the medication processor 56 may activate the drive motor 106. Activation of the drive motor 106 causes the medication 116 to be advanced out of the cartridge 12 (and dispenser 16) to a point where the user may grasp and remove the medication.

In addition to dispensing the medication 116, the medication processor 56, at the same time, may also provide instructions on the use of the medication 116. For example, activation of the ACKNOWLEDGE (or SND) button may cause the medication processor 56 to retrieve the audio file 122 and play the file back for the benefit of the user (e.g., "take this medication with milk", "do not take with aspirin", etc) through an electro-acoustic transducer (e.g., 122).

The medication processor 56 may also retrieve text and/or graphics information from appropriate files 124, 126. The text and/or graphics may be shown on a display 120 (24) as an aid to the user in using the medication. In the case of graphics files, the files may depict an area of the user's body to which the medication is to be applied and graphical instructions as to how to apply the medication.

In addition to dispensing medication and instructing the user on how to use the medication, the dispenser 16 may also monitor and report in the event of failure to take the medication for any reason. In this case, the medication processor 56 may set a flag that activates a compliance processor 57 that, in turn, monitors the medication process for compliance with instructions.

To monitor the medication process, the compliance processor 57 may open and make subsequent entries into a verification of medication file (medication log) 76, 78 each time the medication processor 56 attempts to dispense a medication. The compliance processor may also activate a timer 60 to measure a time in which a user may respond to an alerting message to take a medication. If the user takes too long or does not respond, then the compliance processor 57 may open a non-compliance file 80, 82 and make a corresponding entry noting the lack of response in the file 76, 78.

In this case, the compliance processor 57 may enter an identifier of the user, a time and date 94 of the non-compliance, a drug identifier 96 and a non-compliance indicator 95. The non-compliance indicator 95 may be a numerical value or a text entry indicating a failure of the user to respond to the medication alert. The compliance processor 57 may also provide notification to the user on the display 24, 120 that a medication has been missed.

In addition to monitoring for a response from the user, the compliance processor may also detect the removal and type of medication 116 dispensed. A second timer 60 may be activated upon activation of the actuator 106 to detect a failure of the user to accept the medication.

In this case, a bar code reader 108 may be provided adjacent an exit of the dispenser 12. Upon removal of the medication 116 from the dispenser 16, the bar code reader 108 may read a bar code on a package of the medication 116 and transfer that identification to the compliance processor 57.

Upon receiving the identification, the compliance processor 57 may retrieve the drug identifier 130 from the medication file 72 and compare it to the identifier from the bar code reader 108. If there are any differences, the compliance processor 57 may make a corresponding entry into the non-compliance file 80, 82 and report the difference immediately to the host 20 as a medication noncompliance.

As an alternative, each medication 116 may be provided with a radio-frequency identification (RFID) tag 117. As the medication 116 is removed from the dispenser 16, an RFID transceiver 54 reads an identifier from each RFID tag 117. To prevent the RFID transceiver 54 from reading the tags 117 within the dispenser 12, a radio frequency shield 52 may be provided around the dispenser 12.

As above, the identifier detected by the RFID transceiver 54 is transferred to the compliance processor 57, where the processor 57 compares the identifier with the drug identifier 130 from the medication file 72. Where a difference is found, the compliance processor 57 may make an entry in the non-compliance file 80, 82 and report the difference to the host 20.

In the case where the actuator 106 is activated to deliver medication, but the bar code reader 108 or RFID transceiver 54 fails to detect removal of the medication within the predetermined time period measured by the second timer 60, then the compliance processor 57 may detect the failure as a non-compliance by the expiration of the predetermined time period. In this case, the compliance processor 57 may again make an entry reflecting this situation in the non-compliance file 80, 82 and report the non-compliance accordingly.

If the medication processor 56 activates the actuator 106 to dispense the medication 116 and the compliance processor 57 detects withdrawal of the medication 116 from the dispenser 16, then the medication processor 56 makes an entry into the medication log 76, 78 of the successful dispensing of the medication 116 to the user. The medication processor 56 may note the dispensing of the medication 116 by recording a time and date 84 of the medication and the drug identifier 130 as an entry 86 in the log 76, 78.

The compliance processor 57 may also monitor the amount of medication remaining in the dispenser 12 and send a report to the host 20 when the dispenser is empty or near empty. In this case, the medication file 72 downloaded from the host 20 may include the number of medications that were prescribed and are present within the dispenser 12, or, alternatively, the dispenser 12 may be provided with a memory 110 that contains the initial number of medications 114 along with a drug identifier 112.

In either case, the compliance processor 57 may retrieve the initial value and store the value in a respective remaining medications file 100, 102. After each medication 116 is dispensed, the compliance processor 57 may decrement the number within the file 100, 102. When the remaining number within the file 100, 102 reaches some predetermined minimum value, the compliance processor 57 may notify the user via the display 24, 120 and also send a message to the host 20 notifying the host 20 of the deficiency.

Periodically, or in the event of a non-compliance, the compliance processor 57 may upload some or all of the files 76, 78, 80, 82 to the host 20 along with an identifier of the medication unit 16. In this regard, the compliance processor 57 may retrieve the file 76, 78, 80, 82 and transfer the file to the communication processor 64 where it is encoded for transfer to the host 20. In this case, the file may be incorporated into a message under a TCP/IP format. The communication processor 64 may then transfer the TCP/IP message to a communication channel interface processor 66 where the TCP/IP message may be encapsulated for transfer over the wireless interface to the host 20.

Under one illustrated embodiment of the invention, non-compliance files 80, 82 are transferred immediately upon detection of a non-compliance. For example, a notice indicating that the number of remaining medications 116 within the dispenser 12 is below a threshold value may also be transmitted immediately after detection.

The medication logs 76, 78 may be transferred under control of either the medication processor 56 or compliance processor 57 to the host 20 at regular intervals or upon receiving an information request from the host 20. Upon receipt by the host, the verification of medication files 76, 78 may be archived for later reference.

As an alternative to the host 20 downloading medication files 72, 74 proximate a time of medication, the host 20 may also download medication files 72, 74 for some predetermined future time period (e.g., a week, a month, etc.). In this case, the medication processor 56 periodically scans the medication files 72, 74 and compares a medication time 120 with a time and date from a clock 62. When the medication time 120 matches a clock value, the medication processor 56 may dispense medication as described above.

In addition to accepting acknowledgements to medication alerts, the keyboard 121 (or cellphone 14 of FIG. 1) may also be provided with special function keys to aid the user. For example, one key may be labeled "HELP" or another key may be labeled "DISPENSER EMPTY". If the user should activate a special function key, the communication processor 64 may open a voice or data channel between the user and a healthcare worker at a terminal 22 connected to the host 20.

The healthcare worker may discuss the user's concerns with the user and offer whatever assistance is needed. If the user is confused by the instructions appearing on the display of the dispenser 16, then the healthcare worker may access the user's files 28, 30 within the host 20 and explain in more detail the requirements of the medication. Alternatively, if the dispenser 16 is out of medication or is malfunctioning, the healthcare worker may order a new dispenser 16 or instruct the user as to where to go for service.

The use of the medication compliance system 10 functions to reduce medication non-compliance by significantly reducing the possibility that a user may not understand or may forget his/her medication instructions. The alerting feature functions to remind a user even if the user does not have a watch or forgets the time. The availability of audible alerts or visual displays ensures compliance even with users having impaired cognitive function. The control of the dispensing function by the medication processor also avoids the possibility of the user inadvertently receiving a double dose of medication.

A specific embodiment of method and apparatus for ensuring medication compliance has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention and any and all modifications, variations, or equivalents that fall within the true spirit and scope of the basic underlying principles disclosed and claimed herein.

The invention claimed is:

1. A method of ensuring compliance by a user with a medication program, such method comprising the steps of:
   providing the user with a medication dispensing unit for dispensing medication to the user, said medication dispensing unit having a wireless transceiver operatively coupled to a controller of the medication dispensing unit;

downloading a first set of instructions of a medication routine to the controller of the medication dispensing unit through the wireless transceiver, the downloaded set of instructions being adapted to control the dispensing of medication to the user from the medication unit; and downloading a second set of instructions of the medication routine to the user through the wireless transceiver for presentation to the user concurrent with the dispensing of medication, the downloaded second set of instructions being adapted to instruct the user about how to use the dispensed medication.

2. The method for ensuring compliance as in claim 1 further comprising downloading the first and second sets of instructions through the wireless transceiver from a remotely located server.

3. The method for ensuring compliance as in claim 1 wherein the step of downloading the second set of instructions further comprises verbally presenting the instruction about how to use the medication to the user through an electro-acoustic transducer of the medication unit.

4. The method for ensuring compliance as in claim 1 wherein the step of downloading the second set of instructions further comprises displaying the instructions about how to use the medication on a display of the medication unit.

5. The method for ensuring compliance as in claim 1 further comprising determining a time to dispense the medication based upon the first set of instructions downloaded to the medication unit.

6. The method for ensuring compliance as in claim 5 further comprising dispensing the medication based upon the determined time.

7. The method for ensuring compliance as in claim 6 wherein the step of downloading the first set of instructions further comprises downloading instructions for a plurality of medication dispensing events and executing the medication dispensing events in accordance with a schedule of medication events.

8. The method for ensuring compliance as in claim 6 further comprising activating a medication notification alert based upon the determined time.

9. The method for ensuring compliance as in claim 8 further comprising defining the medication notification alert as an audible alert.

10. The method for ensuring compliance as in claim 8 further comprising defining the medication notification alert as a visual alert.

11. The method for ensuring compliance as in claim 6 further comprising detecting removal of the medication from the dispenser by the patient.

12. The method for ensuring compliance as in claim 11 further comprising detecting an identifier of the medication when the medication is removed from the dispenser by the patient.

13. The method for ensuring compliance as in claim 12 wherein the step of detecting an identifier further comprises reading a bar code from a wrapper of the medication when the medication is removed from the dispenser by the patient.

14. The method for ensuring compliance as in claim 12 wherein the step of detecting an identifier further comprises reading a radio frequency identification tag on the medication when the medication is removed from the dispenser by the patient.

15. The method for ensuring compliance as in claim 12 wherein the step of detecting an identifier further comprising storing the identifier in a medication log along with a time of removal.

16. The method for ensuring compliance as in claim 12 wherein the step of storing the identifier in a medication log further comprises transferring the medication log to the server upon receiving a request from the server.

17. The method for ensuring compliance as in claim 6 further comprising determining a time limit for accepting the medication by the user from the dispenser following the dispensing of the medication.

18. The method for ensuring compliance as in claim 17 further comprising determining that the time limit for accepting the medication has expired and notifying the server of the failure of the user to accept the medication.

19. The method for ensuring compliance as in claim 1 further comprising notifying the user when a medication has been missed.

20. The method for ensuring compliance as in claim 1 further comprising notifying the server when a medication has been missed.

21. The method for ensuring compliance as in claim 1 further comprising notifying the user when the dispenser is empty.

22. The method for ensuring compliance as in claim 1 further comprising notifying the server when the dispenser is empty.

23. A method of ensuring compliance by a user with a medication program, such method comprising the steps of:

providing the user with a medication dispensing unit for dispensing medication to the user and a wireless transceiver operatively coupled to a controller of the medication dispensing unit;

downloading a set of instructions of a medication routine for controlling the medication unit from a server to the controller of the medication dispensing unit through the wireless transceiver; and downloading a set of instructions of the medication routine that instructs the user about how to use the dispensed medication through the wireless transceiver to the user.

24. A medication compliance system for dispensing medication to a user, comprising:

a medication dispenser for dispensing the medication; a cellular controller coupled to the medication dispenser and adapted to dispense the medication under control of instructions downloaded from a medication server through a local cellular communication system; and an audio/visual interface adapted to instruct a user on the use of the dispensed medication in accordance with the instructions downloaded through the local cellular system.

25. The medication compliance system as in claim 24 wherein the medication further comprises a tablet.

26. The system for dispensing medication as in claim 24 wherein the audio/video interface further comprises an audio transducer.

27. The medication compliance system as in claim 24 wherein the audio/video interface further comprises a video display.

28. An medication compliance system for medicating a user, comprising:

a medication dispensing unit provided to the user for dispensing medication to the user;

a wireless transceiver operatively coupled to a controller of the medication dispensing unit;

a first set of instructions of a medication routine downloaded to the controller of the medication dispensing unit through the wireless transceiver, the downloaded set of instructions being adapted to control the dispensing of medication to the user from the medication unit; and a second set of instructions of the medication routine downloaded to the medication dispensing unit through the wireless transceiver for presentation to the user concurrent with the dispensing of medication, the downloaded second set of instructions being adapted to instruct the user about how to use the dispensed medication.

29. The medication compliance system as in claim 28 further comprising a remotely located server that downloads the first and second sets of instructions through the wireless transceiver to the medication dispensing unit.

30. The medication compliance system as in claim 28 further comprising an electro-acoustic transducer for verbally presenting at least a portion of the second instructions about how to use the medication to the user.

31. The medication compliance system as in claim 28 further comprises a display adapted to display at least a portion of the second set of instructions about how to use the medication to the user.

32. The medication compliance system as in claim 28 wherein the first and second sets of instructions further comprise a schedule of medication events for executing a plurality of medication dispensing events over a predetermined time interval.

33. The medication compliance system as in claim 28 further comprising a clock adapted to determining a time to dispense the medication based upon the first set of instructions downloaded to the medication unit.

34. The medication compliance system as in claim 33 further comprising an actuator adapted to dispense the medication based upon the determined time.

35. The medication compliance system as in claim 33 further comprising an alerting device adapted to alert the user to the need for medication.

36. The medication compliance system as in claim 35 further comprising defining the medication notification alert as an audible alert.

37. The medication compliance system as in claim 35 further comprising defining the medication notification alert as a visual alert.

38. The medication compliance system as in claim 33 further comprising a bar code reader adapted to detect removal of the medication from the dispenser by the patient.

39. The medication compliance system as in claim 33 further comprising a radio frequency identification tag reader adapted to detect removal of the medication from the dispenser by the patient.

\* \* \* \* \*